United States Patent [19]

Wampfler

[11] 3,931,304

[45] Jan. 6, 1976

[54] BISMUTH ENHANCED ACTIVITY OF TRANSITION METAL-BROMINE CATALYSIS OF DI- AND TRI-METHYL BENZENE OXIDATION IN LIQUID PHASE

[75] Inventor: Gene L. Wampfler, Lombard, Ill.

[73] Assignee: Standard Oil Company, Chicago, Ill.

[22] Filed: May 21, 1973

[21] Appl. No.: 362,463

[52] U.S. Cl. .............................................. 260/524 R
[51] Int. Cl.$^2$ ......................................... C07C 51/33
[58] Field of Search ............................... 260/524 R

[56] References Cited
UNITED STATES PATENTS

| | | | |
|---|---|---|---|
| 2,833,816 | 5/1958 | Saffer et al...................... | 260/524 R |
| 3,299,125 | 1/1967 | Ichikawa......................... | 260/524 R |

*Primary Examiner*—Lorraine A. Weinberger
*Assistant Examiner*—Richard D. Kelly
*Attorney, Agent, or Firm*—Fred R. Ahlers; Arthur G. Gilkes; William T. McClain

[57] ABSTRACT

Addition of non-transitional bismuth ion to oxidation catalysis provided by heavy, transition metal-bromine ion combination containing both cobalt and manganese ions uniquely increases catalytic activity of said combination for converting ortho substituted methyl groups to corresponding carboxylic acid groups on benzene nucleus by a factor much greater than by the addition of equivalent amount of such high catalytically active heavy, transition metal as cobalt and manganese. Such greater catalytic activity is manifested by longer sustained initial rapid rate of oxygen consumption and higher o-dicarboxybenzene yield.

2 Claims, No Drawings

BISMUTH ENHANCED ACTIVITY OF TRANSITION METAL-BROMINE CATALYSIS OF DI- AND TRI-METHYL BENZENE OXIDATION IN LIQUID PHASE

BACKGROUND OF INVENTION

The possibility of using liquid phase instead of vapor phase oxidation for the preparation of benzene carboxylic acids was first indicated by the disclosure in U.S. Pat. No. 2,245,528 of the catalysis provided by transitional or variable valence metals, especially cobalt, in a liquid phase of saturated lower aliphatic acid at temperatures from 100° to 320°C. and pressures to maintain the liquid phase of the aliphatic acid. Such catalysis, according to said patent, was advantageously promoted by the use of a ketone such as methylethyl ketone or aldehyde such as acetaldehyde. Unfortunately such aldehyde or ketone promoted variable valence metal catalysis was useful only for converting mono-, di- or tri-methylbenzenes to their respective benzene monocarboxylic acids: benzoic, toluic and dimethyl benzoic acids. Two separate, later and somewhat parallel lower temperature (80°–100°C.) modifications of the aldehyde or ketone promoted cobalt catalysis in liquid phase of acetic acid did provide commercially feasible conversion of xylenes to phthalic acids, especially p-xylene to terephthalic acid but only at the expense of using rather high concentrations of cobalt and molar, with respect to p-xylene, quantities of acetaldehyde or methylethyl ketone promoter which were oxidized to acetic acid.

The disadvantages of using high concentrations of cobalt promoted with large quantities of aldehyde or ketone were overcome, and at the same time a greater choice of variable valence metal oxidation catalyst was made available and a wider choice of alkyl-substituted benzene starting materials for benzene di-, tri- and higher carboxylic acids was provided by the discovery of the unique promotional effect on said variable valence metal by bromine ion, provided per se or formed in situ with or without acidic reaction medium provided by $C_1$–$C_8$ monocarboxylic acids having no hydrogens on a tertiary carbon such as benzoic acid and the saturated aliphatic monocarboxylic acids, preferably acetic acid. Such bromine-variable valent metal catalysis, first disclosed in U.S. Pat. No. 2,833,816 also provided, under liquid phase conditions over the temperature range of 120°–275°C., a substantially higher rate of oxidation (e.g., reaction duration of 2 hours or less for conversion of xylenes to high yields of phthalic acids) of alkyl side chains on the benzene ring to nuclear-substituted carboxylic acid groups and was not limited to such oxidative conversion of methyl side chains but rather also applied to much longer side chains. Also the unique effect of bromine ion was not limited to cobalt as variable valence metal but applied in general to polyvalent metals which have atomic weights in the range between 50 and 200. Such unique effect of bromine was most promounced when used in combination with cobalt, manganese, cerium (the metals of known highest oxidation potential) and with combinations of two or more of those polyvalent metals. Combinations of cobalt and manganese became preferred for commercial use. However, said patent also indicated that bromine had some unique effect on metals normally considered as having valencies which are non-variable. For example, use of bromine-bismuth catalysis caused selective oxidation of the isopropyl-substituent of p-cymene to the exclusion of oxidation of the methyl-substituent to yield p-toluic acid.

The bromine-polyvalent metal catalysis in acetic acid solvent has been in commercial use in many countries for the manufacture of terephthalic acid from p-xylene for more than 14 years and has progressed to the point of producing a crude terephthalic acid product of 99.5–99.6 weight percent purity in yields of 94–96 percent of theory in reaction durations of 40–60 minutes. But, in the absence of acetic acid solvent, best yield of a single phthalic acid (e.g., terephthalic acid) on a once through basis of the xylene amounted, according to U.S. Pat. No. 2,833,816 to about 20 weight (12.8 mole) percent. Most development attention to achieve such high commercial yields and quality has been given to the catalysis afforded by combinations of bromine with mixtures of cobalt and manganese as polyvalent metal components of the catalysis. However, no attention has been given to the effect on such otherwise highly effective catalysis by metals whose valencies, in general, have been considered to be non-variable in spite of earlier indications that bromine, unique of the promoters, tended to promote them from no activity to some activity as oxidation catalysts.

INVENTION SUMMARY

For liquid phase oxidation of di- and trimethylbenzenes having ortho methyl groups with molecular oxygen it has been discovered that bismuth is unique among the Group VA metals for substantially enhancing the activity of the bromine-manganese-cobalt system of catalysis. There are two aspects of the enhancement by bismuth. The first is an increase in activity of Mn-Co-Br system of catalysis by a factor much greater than would be expected by increase of amounts of either Mn and/or Co equivalent to the amount of bismuth employed. The second is manifested by the longer sustained initial rapid rate of oxygen consumption when bismuth is a member of the systems of catalysis than when the catalysis systems comprise Mn-Co-Br.

Such functions of bismuth are indeed unobvious when the character and nature of it are considered and compared to Mn and/or Co which have been known for some time to have the highest oxidation potential of the transition metals characterized in U.S. Pat. No. 2,425,528 as oxidation catalysts. Bismuth is not generally considered to be a transition metal in a redox system as are Co, Mn and other of such heavy metal oxidation catalysts because of its non-variable valence state in oxidation systems.

It is appreciated that combinations of cobalt with Group IIIA or Group IVA metals (also Bi) without alkyl side chain oxidation initiators or promoters are taught in U.S. Pat. No. 3,299,125 as beneficial systems of catalysis for the liquid phase oxidation of alkyl-substituted aromatic hydrocarbon containing 2 or more alkyl groups which are not nuclear substituted on carbons in ortho positions with respect to each alkyl group. Thus the Co-Bi system of catalysis is taught as ineffective for di- and trialkylbenzenes such as o-xylene or pseudocumene (1,2,4-trimethylbenzene).

It is further appreciated that U.S. Pat. No. 3,562,318 teaches for liquid phase oxidation of alkyl-substituted aromatic compounds in the presence of aldehyde or ketone side chain oxidation initiators or promoters the beneficial effect of cobalt in combination with one or more metals of the group consisting of Al, Zr, La, Nd, Zn, B or Mg.

Canadian Pat. No. 829,343 further adds for the ketone or aldehyde side chain oxidation initiation or promotion of liquid phase oxidation of alkyl-substituted aromatic hydrocarbons, the beneficial effect of cobalt-niobium system of catalysis.

According to each of the foregoing prior teachings, very high levels of cobalt concentrations are required in the liquid phase containing acetic acid as reaction solvent. But, even then, the oxidation rates are inordinately slow and make the disclosed combinations of systems of catalysis commercially unattractive. Such systems of catalysis are even more unattractive commercially when compared against the most widely used, on a world-wide basis, commercial catalysis which uses relatively low concentrations of components of the Co-Br and Mo-Co-Br systems of catalysis resulting in tere- or isophthalic acid yields 92–95 mole percent of a purity of 99–99.5% from oxidations conducted on a continuous basis with xylene residence time in the range of 40–50 minutes.

In such continuous operations the catalysis components are used in the range of 1.0 to 2.0 milligram atoms of total metal (i.e., total of Co or Mn or Co and Mn as the metals although charged as metal salts) and 1.0 to 2.0 milligram atoms of bromine (calculated as the element although charged as a bromine-containing compound) per gram-mole of p- or m-xylene. The oxidation of di- and trimethyl substituted benzenes having two nuclear substituted methyl groups (i.e., o-xylene and pseudocumene) require slightly higher total concentrations of the metals Co and Mn and higher concentrations of bromine. Thus for o-xylene oxidation the total concentration of metals (Co, Mn or Co-Mn) are 2.0 to 4.0 milligram atoms and the bromine concentrations are also 2.0 to 4.0 milligram atoms per gram-mole of o-xylene. For pseudocumene oxidation the total metals (Co, Mn and Co-Mn) concentration is 2.25–5.0 milligram atoms and bromine concentration is 4.5–10.0 milligram atoms per gram mole of pseudocumene.

SPECIFIC EMBODIMENTS

For the present invention oxidation of o-xylene or pseudocumene the ratio of bismuth to total conventional metal oxidation catalysts (Mn-Co) is in the range of respective metals (i.e., Bi: total conventional metals) of 0.1–1.0:1.0 on a milligram-atom basis. The ratio of total metals, Bi plus conventional oxidation metals to bromine, is in the range of 0.5 to 3.0:1.0 on the milligram atom basis. As will be hereinafter demonstrated, to obtain the unique effects of bismuth the conventional metal oxidation catalyst must contain both cobalt and manganese.

Bismuth can be added to the reaction in any form soluble in o-xylene being oxidized or in acetic acid when it is being used as reaction solvent. For example, bismuth octanoate or naphthanate can be used with manganese and cobalt octanoates or naphthanics for oxidation of o-xylene in the absence of reaction solvent and each of Bi, Mn and Co can be conveniently used as their acetates when o-xylene is oxidized in the presence of acetic acid solvent.

The source of molecular oxygen for the Bi enhanced oxidation of this invention can vary in $O_2$ content from that of air to oxygen gas. Air is the preferred source of molecular oxygen for oxidations conducted at temperatures at 150° and above up to 275°C. For oxidations conducted with molecular oxygen the preferred temperatures are in the range of 130° to 200°C. The minimum pressure for such oxidations is that pressure which will maintain a substantial liquid phase 70–80%, of the reaction medium either neat o-xylene or o-xylene and 70–80% of the acetic acid. The acetic acid solvent, when used, can amount to 1–10 parts on weight basis per part of o-xylene. The o-xylene and/or acetic acid not in the liquid phase because of vaporization by heat of reaction is advantageously condensed and the condensate returned to the oxidation as a known means for removing heat and thereby temperature controlling the exothermic oxidation reaction. Such vaporization of o-xylene reactant and/or acetic acid solvent is also accompanied by vaporization of lower boiling by-product water. When it is desired to take advantage of the known benefits of control of water concentration in oxidation, condensed water is separated from the condensate before its return to the oxidation reaction by any one of the well known means for accomplishing such separation of water. For example, by phase separation of liquid water from o-xylene condensate or by distillative separation of water from acetic acid.

The benefits to be derived from the use of bismuth according to the present invention are indicated by results shown with respect to the following illustrative and comparative oxidations using o-xylene as reactant and acetic acid as reaction solvent.

In the examples to follow all oxidations are conducted at a gauge pressure of 300 pounds per square inch (psig) and at oxidation initiation temperature of 350°F. using a weight ratio of acetic acid to xylene of 3:1 and using air as the source of molecular oxygen. The oxidation reactor used in an unstirred titanium tubular reactor having an internal diameter of 1.0 inch and a height of 36 inches of which the upper portion is a water cooled condensation zone. Following the condensation system, there are means for venting the exhaust gaseous mixture (nitrogen, unused or excess oxygen, oxides of carbon, water vapor, and vapor of uncondensed acetic acid) and analytical means for determining the oxygen, carbon dioxide and carbon monoxide contents of exhaust sample on acetic acid-free dry basis. The exhaust sample flows through a super-cooled (e.g., dry ice-acetone cooled) trap before analysis for $O_2$, $CO_2$ and CO. The reactor is charged with 50 grams xylene, thus 150 grams acetic acid for said 3:1 solvent to o-xylene weight ratio. The oxidation of o-xylene is conducted batchwise by charging all of the catalyst components, o-xylene and acetic acid to the reactor. The reactor is sealed. The pressure control valve is set at 300 psig (valve is in exhaust vent line). The reactor is pressured to 300 psig with nitrogen and then heated to 350°F. Thereafter pressurized air is introduced into the liquid phase in the reactor. Cooling water at 50°F. is introduced into the jacket of the condenser section. Each oxidation is terminated as close to 10% oxygen by volume as is feasible to do. It will be understood that the oxygen content in the exhaust gas (dry and free of acetic acid) can rapidly increase when oxidation ceases. The attempted termination of oxidation at 10% oxygen (about half-way to oxygen content of air) is for the purpose of determining the effect of bismuth during the most rapid oxygen consumption by the methyl-substituted benzene reactant because thereafter, even though oxygen concentration is maintained at a substantially constant concentration in the liquid phase, oxygen consumption naturally diminishes directly with disappearance of oxidizable substituents on the benzene ring and catalytic effect becomes more difficult to evaluate.

After termination of the oxidations, the total reactor effluents (hereafter "TRE") are drained and collected. The reactor for the o-xylene oxidations is washed with acetic acid and each wash is combined with its respective TRE. The resulting TRE products are submitted for polarographic, neutrals and aromatic acid analysis.

Product yields are calculated (and hereafter reported) in mole percent of product per mole xylene charged.

Other pertinent details of the illustrative oxidations and the results so produced are presented hereafter in Tables I–IV. Bismuth tribromide is used as the source of both bismuth and bromine in the systems of catalysis Bi-Mn-Br, Bi-Co-Br, Bi-Co-Mn-Br, and Bi-Br. However other sources of bismuth and bromine can be used, for example bismuth triacetate and ammonium bromide, hydrogen bromide, sodium bromide, elemental bromine, benzyl bromide, tetrabromoethane, and others within the teachings of U.S. Pat. No. 2,833,816. Cobalt and manganese are used as their acetate tetrahydrates and, when no Bi is present, the bromine source is tetrabromoethane. For the present inventive catalysis system Bi-Co-Mn-Br, the metal sources can be any form of the metal which dissolves in acetic acid solvent and need not be only the acetate or bromide salts of the respective metals. Also the source of bromine can be those bromine compounds other than bromide salts of the metals in said system.

tive catalysis for oxidation. To achieve substantially the same o-phthalic acid yield and total oxygen uptake as in illustrative Example 1 which uses Bi-Co-Mn-Br as catalysis system, the system Co-Mn-Br must have 5.3 mgatom Co and 1.7 mgatom Mn per gram mole o-xylene to replace 1.0 mgatom of Bi even though Co and Mn are known to be highly effective oxidation catalysts and are capable of having two different oxidation states in a redox system. It is indeed surprising that 1.0 gmatom Bi per gram mole of o-xylene appears to be equivalent to a total of 7 gmatoms of Co and Mn per gram mole o-xylene when Bi in solution forms only covalent compounds and has only a single oxidation state and thus is considered to be a non-varient valent metal. The use of Bi in the system Bi-Mn-Br or Bi-Co-Br does not (compare Examples B and C with illustrative Example 1) manifest such surprising effect.

Data for illustrative Example 2 (oxidation terminated at 36 minutes at 10.1 vol. % $O_2$ in vent) is given to show that a substantial portion of molecular oxygen for completion of the oxidation (see illustrative Example 1) taken up in the 36 minutes thus illustrating the other unique effect of Bi to sustain oxygen uptake. Comparative Example E is given to demonstrate the Co-Mn-Br system containing the same concentration of said components on o-xylene as in Example 1. The results of Example E compared to results of Example 1 demonstrates again the unique effect of only a small amount of Bi.

The same surprisingly unique effect of Bi in the catalysis system Bi-Co-Mn-Br is not manifest in the oxidation of xylenes having no orthomethyl groups as m- and

TABLE 1

| | BISMUTH EFFECT ON ORTHO-XYLENE OXIDATION | | | | | | |
|---|---|---|---|---|---|---|---|
| Example | A | B | C | D | 1 | 2 | E |
| mg atom Bi/gm mole o-xylene | 0 | 1.5 | 1.5 | 3.0 | 1.0 | 1.0 | 0 |
| mg atom Co/gm mole o-xylene | 6.3 | 0 | 1.5 | 0 | 1.0 | 1.0 | 1.0 |
| mg atom Mn/gm mole o-xylene | 2.7 | 1.5 | 0 | 0 | 1.0 | 1.0 | 1.0 |
| mg atom Br/gm mole o-xylene | 9.5 | 4.5 | 4.5 | 9.0 | 3.0 | 3.0 | 2.0 |
| Total mg atom metals/mg atom Br | 0.95 | 0.67 | 0.67 | 0.33 | 1.0 | 1.0 | 1.0 |
| Conditions: | | | | | | | |
| Average temperature, °F. | 406 | 409 | 410 | 414 | 412 | 412 | 411 |
| Oxidation time, minutes | 37 | 16 | 16 | 13 | 46 | 36 | 24 |
| Final % $O_2$ in vent | 10.0 | 10.9 | 10.1 | 19.1 | 18.6 | 10.1 | 10 |
| Results: | | | | | | | |
| $O_2$ uptake, liters | 38.2 | 13.5 | 13.0 | 0 | 37.1 | 30.8 | 21.8 |
| Liter $CO_2$/liter $O_2$ | 0.140 | 0.073 | 0.174 | 0 | 0.073 | 0.119 | 0.100 |
| Molar yields, % | | | | | | | |
| o-Phthalic acid | 78.3 | NA[4] | NA[4] | None | 79.3 | | 15.0 |
| 2-Carboxybenzaldehyde | 0.8 | " | " | " | 0.6 | | 7.2 |
| o-Toluic acid | 0.4 | " | " | " | 0.6 | | 35.1 |
| Phthalide | 0.4 | " | " | " | 1.0 | | 9.8 |
| Total intermediates[1] | 3.0 | " | " | " | 3.0 | | 63.6 |
| C-7 Aromatics[2] | 0.5 | " | " | " | 1.5 | | 0.7 |
| C-9 Aromatics[3] | 0.3 | " | " | " | 0.2 | | 1.5 |

[1]Sum of o-xylene, o-tolualdehyde, o-phthalaldehyde, o-methylbenzyl alcohol, o-toluic acid and 2-carboxybenzaldehyde.
[2]Sum of benzaldehyde and benzoic acid.
[3]Sum of methyl dibasic acids, trimellitic acid and trimesic acid.
[4]NA— Not Analyzed.

From the data in TABLE I it will be noted from Example D that the system Bi-Br does not provide effective p-xylene. This can be illustrated by the three oxidations of p-xylene shown in Table II.

TABLE II

| EFFECT OF BISMUTH ON PARA-XYLENE OXIDATION | | | |
|---|---|---|---|
| Example | F | G | H |
| mgatom Bi/gm mole p-xylene | 0 | 0.10 | 0.25 |
| mgatom Co/gm mole p-xylene | 0.25 | 0.25 | 0.25 |
| mgatom Mn/gm mole p-xylene | 0.75 | 0.75 | 0.75 |
| mgatom Br/gm mole p-xylene | 1.0 | 1.10 | 1.25 |
| Total mgatoms metal/mgatom Br | 1.0 | 1.0 | 1.0 |
| Conditions: | | | |
| Average temperature, °F. | 412 | 408 | 407 |
| Oxidation time, minutes | 100 | 114 | 106 |
| Final $O_2$ % in vent | 18.0 | 18.0 | 18.0 |

TABLE II-continued
EFFECT OF BISMUTH ON PARA-XYLENE OXIDATION

| Example | F | G | H |
|---|---|---|---|
| Molar Yields, % | | | |
| Terephthalic acid | 96.3 | 96.4 | 33.0 |
| p-Toluic acid | 1.0 | 1.0 | 45.9 |
| 4-Carboxybenzaldehyde | 1.3 | 1.4 | 11.3 |
| Total intermediates | 2.4 | 2.4 | 57.9 |
| C-7 Aromatics | 0.6 | 0.9 | 2.3 |
| C-9 Aromatics | 0.5 | 0.2 | 6.6 |
| Optical Density of Product: | | | |
| at 340 nm | 2.26 | 3.04 | 3.68 |
| at 400 nm | 0.16 | 0.24 | 0.29 |

From the foregoing data the use of the system Bi-Co-Mn-Br (Example G) as compared to the system Co-Mn-Br (Example F) shows Bi to have no adverse effect at Bi/Co of 1:4 except to produce a product of slightly higher color as indicated by the optical density values. However at higher Bi/Co ratio of 1.0:1.0 the system Bi-Co-Mn-Br had a rather adverse effect on the oxidation by lowering terephthalic acid product yield to about one-third of that obtained in the absence of Bi and produced a more colored product.

What is claimed is:

1. A method of preparing o-phthalic acid or trimellitic acid by oxidizing o-xylene or pseudocumene with molecular oxygen at a temperature in the range of 130° to 275°C in the presence of acetic acid under a pressure to maintain acetic acid in the liquid phase at such temperature, the improvement comprising the use of catalysis provided by the components consisting essentially of bismuth, bromine and the variable valence metals cobalt and manganese wherein said variable valence metals are present in the amounts of from 2 to 5 milligram atoms and bromine is present in amounts of from 2 to 10 milligram atoms, each on a per gram mole of o-xylene or pseudocumene basis and the ratio of bismuth to said variable valence metals is from 0.1 to 1.0:1.0 milligram atom basis.

2. The method of claim 1 for the preparation of o-phthalic acid by the oxidation of o-xylene with air in the presence of liquid acetic acid solution of the components of catalysis wherein for each gram mole of o-xylene there is present 1.0 milligram atom of each of Bi, Co and Mn.

* * * * *